United States Patent [19]

Houck et al.

[11] Patent Number: 4,571,336

[45] Date of Patent: Feb. 18, 1986

[54] IMMUNE STIMULATION

[75] Inventors: John C. Houck; Leonard M. Patt, both of Seattle, Wash.

[73] Assignee: Endorphin, Inc., Seattle, Wash.

[21] Appl. No.: 694,899

[22] Filed: Jan. 25, 1985

Related U.S. Application Data

[63] Continuation of Ser. No. 526,356, Aug. 25, 1983, abandoned, which is a continuation-in-part of Ser. No. 419,995, Sep. 20, 1982, abandoned.

[51] Int. Cl.[4] .................. A61K 37/02; A61K 35/26; C07G 7/026
[52] U.S. Cl. ........................................ 424/95; 514/2; 514/21; 260/112 R
[58] Field of Search ............. 514/21; 424/95; 260/112 R

[56] References Cited

U.S. PATENT DOCUMENTS

| | | | |
|---|---|---|---|
| 4,002,602 | 1/1977 | Goldstein | 424/177 |
| 4,239,498 | 12/1980 | Rule | 260/112 R |
| 4,250,084 | 2/1981 | Trainin | 260/112 R |
| 4,377,511 | 3/1983 | Lopukhin et al. | 260/112 R |

OTHER PUBLICATIONS

Kook et al., *Cellular Immunology*, 19, 151–157 (1975).
Dardenne et al., *J. Biol. Chem.*, 252:22, 8040–8047 (1977).
Bach et al., *Transplant Proc.*, XIV:3, 509–512 (1982).
Low et al., *Ann. N.Y. Acad. Sci.*, 332, 33–48 (1979).
Goldstein, *Nature*, 247, 11–14 (1974).
Schlesinger et al., *Cell*, 5, 367–370 (1975).
Watson et al., *J. Exp. Med.*, 150, 849–858 (1979).
Gillis et al., *J. Immunol.*, 124:4, 1954–1962 (1980).
Mier et al., *Proc. Natl. Acad. Sci. USA*, 77:10, 6134–6138 (1980).
Di Sabato, *Proc. Natl. Acad. Sci. USA*, 79, 3020–3023 (1982).
Savage et al., *J. Biol. Chem.*, 247:23, 7609–7611 (1972).
Ruscetti et al., *Blood*, 57:3, 379–394 (1981).
Nishioka et al., *Biochem. Biophys. Res. Comm.*, 47:1, 172–179 (1972).
Broome et al., *J. Exp. Med.*, 138, 574–592 (1973).
Hardt et al., *J. Exp. Med.*, 154, 262–274 (1981).
Hadden, in *The Pharmacology of Immunoregulation*, 1978, 369–383.

*Primary Examiner*—Donald B. Moyer
*Assistant Examiner*—Jacqueline M. Stone
*Attorney, Agent, or Firm*—Burns, Doane, Swecker & Mathis

[57] ABSTRACT

Immunostimulatory peptide is isolated from bovine thymus tissue and is useful to treat mammals and birds at risk from viral or fungal infections or other trauma.

4 Claims, 7 Drawing Figures

IMMUNE STIMULATION

RELATED APPLICATION

This application is a continuation of application Ser. No. 526,356, filed Aug. 25, 1983, now abandoned, which was a continuation-in-part application of Ser. No. 419,995, filed Sept. 20, 1982, now abandoned.

BACKGROUND OF THE INVENTION

Mammals and birds, particularly commercial poultry flocks, are often at risk due to exposure to various viral or fungal infections. Such exposure can arise in the natural environment, particularly the dairy or poultry farm, or from unusual situations such as surgery, accidents or wounds. The mammalian body defends against viral and fungal infections by an immunological sequence of events stimulated by the presence of the invasive entity such as virus, bacteria or fungus, the end result of which is the production of T-cells which act in conjunction with macrophages to promote phagocytosis.

Some mammals are deficient in this immunological response either because of some metabolic malfunction, or due to medical treatment such as chemotherapy or spleenectomy. Many domestic animals, particularly poultry, seem to be constantly susceptible to such infections and do not respond immunologically with sufficient rapidity to prevent the loss of large numbers of them. Turkey flocks are especially sensitive in this regard. This leads to significant increases in the costs of turkey husbandry.

A material to enhance the immunological response of mammals to infection would be an important addition to the armamentarium of the physician or veterinarian. Such a substance could be used prophylactically with subjects constantly exposed to infection, defensively with subjects about to undergo surgery, or supportively to improve the immunological response of subjects already suffering from an active infection or recovering from surgery or other trauma.

SUMMARY OF THE INVENTION

It has now been discovered that an immunostimulatory factor utilizable to achieve these results can be isolated from bovine thymus tissue.

This factor has a number of distinguishing characteristics by which it can be identified and distinguished from other stimulatory factors which have been described, including some which have been found in thymus tissue. Among these characteristics are the following:

1. It is amphoteric and strongly adheres to Sephadex and BioGel-P at both neutral and slightly acid pH.
2. Its isoelectric point is from 7.0 to 7.8.
3. It stimulates the DNA-synthetic response of both murine and human lymphocytes to alloantigenic stimulation in mixed lymphocyte culture (MLC).
4. It does not significantly increase the stimulation of splenic murine lymphocytes by lipopolysaccharide from *Salmonella typhosa (LPS)*.
5. There is no decrease in its immunostimulatory activity in the presence of 2-mercaptoethanol.
6. Its stimulatory activity is fully reversible.
7. It functions more effectively in MLC medium containing human serum than in such medium containing fetal serum.
8. Its stimulatory activity in MLC is not affected by the presence of mouse serum.
9. It will accelerate the rejection of histoincompatible skin grafts in mice.
10. On dialysis through dialysis tubing with a 3500 Daltons cut-off, it passes through the tubing.
11. On gel filtration at pH 10.2 in 0.05M ammonium hydroxide, it splits into two immunostimulatory fractions, one with a molecular weight of about 1400 Daltons and the other less than 1400 Daltons but more than 100 Daltons.

The immunostimulatory factor of this invention is useful to stimulate the resistance of the mammalian or avian body to infection either as a preventative measure or as a curvature measure.

DESCRIPTION OF THE INVENTION

The immunostimulatory factor of this invention has been isolated from bovine thymus tissue, specifically frozen calf thymus or dried, defatted calf thymus. The latter material is available from Viobin Corporation, Monticello, Ill.

In the first step of the isolation procedure, thymus tissue from either source in cut into small pieces, e.g. 1 cm² and homogenized into 3 to 4 volumes of ice cold buffer at about 0° to 5° C. at pH 7 to 9, for example, 50 mM ammonium carbonate, pH 8.5 in a Polytron homogenizer for two minutes at low speed and two minutes at high speed. The homogenate is centrifuged at 26,000 to 30,000×G for 20 to 40 minutes at about 0° C. to 5° C., preferably 28,000×G for 30 minutes, and the resulting supernatant solution removed. The pellet is re-extracted as above and the pooled supernatants lyophilized. The lyophilized powder is suspended in water at about 0° C. to 5° C. at a concentration of 0.2 to 0.3 gm/ml and absolute ethanol is slowly added at the same temperature while stirring to a final concentration of 50% to 60% (V/V). The solution is stirred for 16 to 18 hours at 0° to 5° C. followed by centrifugation at the same rates and times mentioned above. The resulting clear supernatant is slowly added to 5 to 6 volumes of acetone precooled to about −5° to −10° C. and maintained at −5° C. to −15° C. for 3 to 6 days. The precipitate is isolated, e.g. by centrifugation or filtration, resuspended in 100 to 200 ml of distilled water or in the same amount of 20 mM acetic acid and lyophilized at 0° to 5° C.

The material isolated by this procedure is normally a light tan sticky powder which contains the stimulatory factor of this invention as well as a number of inhibitory factors and other materials. The desired factor can be isolated from this fraction by gel filtration or by ion exchange chromatography. For convenience, it is referred to herein as the CTE-acetone precipitate.

The various procedures utilized in isolating, characterizing and establishing the utility for the stimulatory factor of this invention will now be discussed.

GEL FILTRATION

Figure 1:
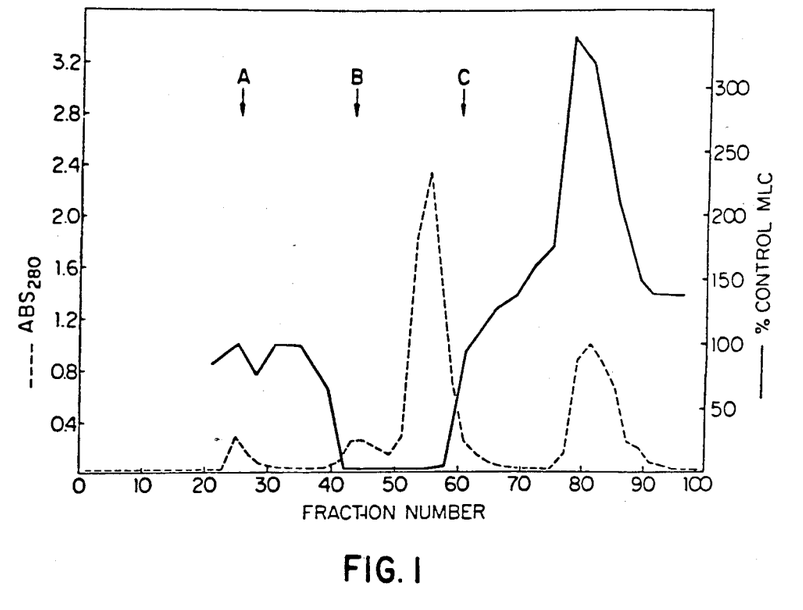
FIG. 1 is a Sephadex G-25 column profile of a calf thymus extract acetone precipitate. Fractions were screened for absorbance at 280 nm ( - - - ) and for activity in a murine MLC (—). The marker A indicates the elution position of bovine serum albumin; B, bacitracin; and C, sodium chloride.

In one gel filtration procedure CTE-acetone precipitate is passed over Sephadex G-25 in a 90×2.2 cm column equilibrated with an acidic lyophilizable buffer at a pH of from 4 to 5 such as 0.1M acetic acid, 100 mM pyridine acetate, pH 4.5 or 0.1M ammonium acetate, pH 5.0. Two milliliter fractions are collected and assayed by MLC. The results with the pyridine acetate are shown in FIG. 1.

Other gel filtration procedures are carried out on a 1×45 cm column of Sephadex G-50 in phosphate buffered saline, (PBS) 0.02M phosphate, 0.15 sodium chloride, pH 7.4 and a 1×45 cm column of BioGel P-10 in 0.5M ammonium bicarbonate, pH 8.0.

For molecular weight determinations, the pooled stimulatory fractions from a G-25 column are passed over a selected BioGel column of the same dimensions at pH 10.2 in 0.05M NH₄OH and eluted with the same reagents.

The Sephadex products are a well known series of cross linked dextrans available from Pharmacia Fine Chemicals, Inc. of Piscataway, N.J. They are widely employed for the separation of natural materials. As normally utilized, the selected Sephadex is packed in a column, a solution containing the dissolved material to be analyzed is passed over the column and eluted with a selected solvent or series of solvents. Each specific Sephadex will separate materials of a specific molecular weight range. Dissolved materials above that molecular weight range will pass through the column in solution in the solvent front - - - the so called void volume. Materials which are retained will be successively eluted as more and more solvent is passed through the column. They will elute in order of progressively decreasing molecular weights.

Sephadex G10 will separate materials with molecular weights of from 200 to 700 Daltons.

Sephadex G-25 will separate materials with molecular weights of from 5000 to 1000 Daltons.

Sephadex G-50 will separate materials with molecular weights of from 30,000 to 1,500 Daltons.

BioGel P is a series of porous polyacrylamide beads used for high resolution gel filtration in a manner similar to Sephadex Gels. Available from Bio-Rad Laboratories, Richmond, Calif.

The ranges for the various species are as follows:
BioGel P-10 will separate 20,000 to 1,500 Daltons.
BioGel P-4 will separate 4,000 to 8,000 Daltons.
BioGel P-2 will separate 1,800 to 100 Daltons.

All gel filtration columns are calibrated with standards of known molecular weight and with sodium chloride. The standards employed in the procedures described herein are:

| bovine serum albumin | 68,000 Daltons |
| cytochrome C | 12,000 Daltons |
| bacitracin | 1,400 Daltons |

The standards are detected either by absorbance at 280 nm or by reaction with ninhydrin. The elution position of sodium chloride is determined by precipitation with acidic silver nitrate. The sodium chloride gives the position of the smallest molecules eluted from the column. In normal usage, all fractions below the lowest fractionation range will elute together with the sodium chloride.

ION EXCHANGE CHROMATOGRAPHY

Small scale ion exchange columns are prepared using Bio-Rad, AG-50 WX8 and AG-1-X8 resins, ammonia and acetate forms respectively. The resins are washed extensively and equilibrated with 10 mM ammonium acetate, pH 7.0. Small columns of approximately 8 ml volume are prepared in 10 ml plastic syringes fitted with Luer-lok valves. For analysis of the ionic nature of the stimulatory factor, 150 mg of the acetone precipitated product described above is dissolved in distilled water such that the conductivity is less than the 10 mM ammonium acetate, and the pH adjusted to 7 to 7.5. One third of this solution is applied to each column, while the remainder serves as a control. The sample is run slowly through the column, and the column is washed with 5 column volumes of 10 mM ammonium acetate, pH 7.0. The unretained fraction is lyophilized, redissolved in distilled water, again lyophilized, and subjected to MLC assay.

Bio-Rad AG-resins are crosslinked polystyrene beads in which some of the phenyl moieties are substituted with ionic functional groups. AG-50 is a strong cation exchange resin with sulfonic groups. AG-1 is a strong anion exchange resin with quaternary ammonium substituents. They are available from Bio-Rad laboratories.

Large scale ion exchange chromatography is performed on a 1×30 cm column of AG 50 WX8 resin, ammonia form, equilibrated with distilled water. Pooled samples of stimulatory composition from a G-25 column are dissolved in distilled water and adjusted to low conductivity and a pH of 5 to 6 with 0.01 acetate buffer. The column is eluted with a gradient made by mixing 90 ml each of distilled water and 1M ammonium hydroxide. Fractions of approximately 2 ml are collected, lyophilized, and assayed for activity by MLC.

DIALYSIS

Dialysis is performed using Spectrapor-3 dialysis tubing (Spectrum Medical Industries, Inc. 60916 Terminal Annex, Los Angeles 90054) with a manufacturer's determined molecular weight cut-off of 3,500 Daltons. At equilibrium, molecules with a molecular weight greater than 3,500 Daltons are retained within the dialysis bag (the Retentate) and those of molecular weight less than 3,500 Daltons will pass through the bag (the Dialysate). The relative amounts of activity at equilibrium will be in proportion to the relative volumes of each fraction, in these experiments 30 ml of Retentate to 300 ml of Dialysate. For a less than 3,500 molecular weight component, approximately 10% would be expected to be found in the Retentate and 90% in the Dialysate.

MIXED LYMPHOCYTE CULTURE (MLC)

The spleen is sterilly removed from C57/BL and Balb/C mice and placed in a Petri dish containing cell collection media (Earl's Balanced Salt solution containing 2.5% heatinactivated fetal calf or human serum, 100 U/ml penicillin, 100 μg/ml streptomycin and 100 IU/ml heparin). The spleen is perfused briefly using a 22- or 25-gauge needle to remove red blood cells, placed in a second dish, and teased gently to remove the spleen lymphocytes. The large pieces are removed through a 50-mesh screen and the lymphocytes are recovered by centrifugation at 200 G for 10 minutes. The cells are washed once with cell collecting media and resuspended incomplete assay media (Minimum Essential Media, Gibco), 5% or 10% heat inactivated human or fetal calf serum, and $5\times10^{-4}$M 2-mercaptoethanol. Human peripheral blood lymphocytes are obtained from blood donated by healthy laboratory personnel. Blood is defibrinated by shaking with glass beads and lymphocytes obtained by centrifugation through a Ficole-Hypaque cushion. The lymphocytes collect at the interphase, are washed by centrifugation with Earl's Balanced Salt Solution (Gibco) and suspended in complete assay media without added 2-mercaptoethanol.

Two-way MLC are set up by adding $1.25\times10^5$ cells/well from each strain or donor to microwell plates (Falcon No. 3040 or Linbro No. IS-FB-96). The plates are incubated at 37° C. for four days. Tritiated thymidine (0.5 μCi, 2Ci/nmole) is added for the last six hours of the culture period. At the end of the culture period, the extent of blast cell formation is obtained by microscopic examination of the plates. The cells are harvested using a Satron cell harvester, and the amount of radioactive label incorporated determined. The incorporation of $^3$H-thymidine in control murine MLC in 10% human serum is 30,000 cpm per well with an average standard deviation in all samples of 10% or less of the total incorporation determined. The incorporation of $^3$H-thymidine is a measure of blast cell formation and therefore a measure of immunological response.

MITOGEN STIMULATION

For stimulation of various lymphocyte sub-populations by lectins, spleen cell suspensions are prepared as above and 250,000 cells of one strain are placed in each well. Experimentally determined optimum amounts of mitogens are added and the incubations continued for 72 hours. The lectins used are Con A (Difco, 0.1 μg/well), Phytohemaglutinin-M (PHA-M, Difco, 20 μg/well) and lipopolysaccharide from *Salmonella typhosa* (LPS, Sigma, 1.5 μg/well). The extent of blast cell formation and label incorporation are measured by the same procedures as described for MLC.

SKIN GRAFTS

For this in vivo study of immune response, C57/BL recipients were grafted with full thickness grafts obtained from histoincompatible Balb/C mice. Grafts of about 1 cm$^2$ are obtained from Balb/C donors and sutured at the corners to prepared beds on the backs of groups of six C57/Bl recipients under Halothane anesthesia. The grafts are inspected daily both visually and tactily starting on the sixth day after grafting. One set of animals is preimmunized by grafting and rejecting a similar transplant one month prior to the final experiment. Statistical analysis is in accordance with students' t-test for paired populations.

The results of the studies described above will now be described in detail so that those skilled in the art will recognize the characterizing features of the immunostimulatory factor of thsi invention.

The biological activities present in the CTE-acetone precipitate were resolved by gel filtration on columns of Sephadex G-25. The entire effluent of the column was screened by determining the effect of the various fractions on murine MLC in human serum. The use of human serum to culture the lymphoid cells was observed to be essential to avoid the strong inhibitory effects of polyamines present in the tissue extracts.

The results of the screening with pyridine acetate buffer at pH 4.5 are shown in FIG. 1 from which it will be seen that the inhibitory factor is eluted just after the bacitracin marker at a $K_{AVE}$ of 0.76.

The stimulatory factor elutes immediately behind the salt at a $K_{AVE}$ of 1.33 near a large 280 nm absorbing peak. The yield of stimulatory material obtained by this procedure was about 1.5 mg for each 1000 mg of CTE-acetone precipitate applied to the column.

Similar results were obtained with commercial defatted calf thymus.

From the elution position of the stimulatory factor it is clear that it must interact or adsorb strongly to Sephadex G-25 under the elution conditions as described above.

Figure 2:
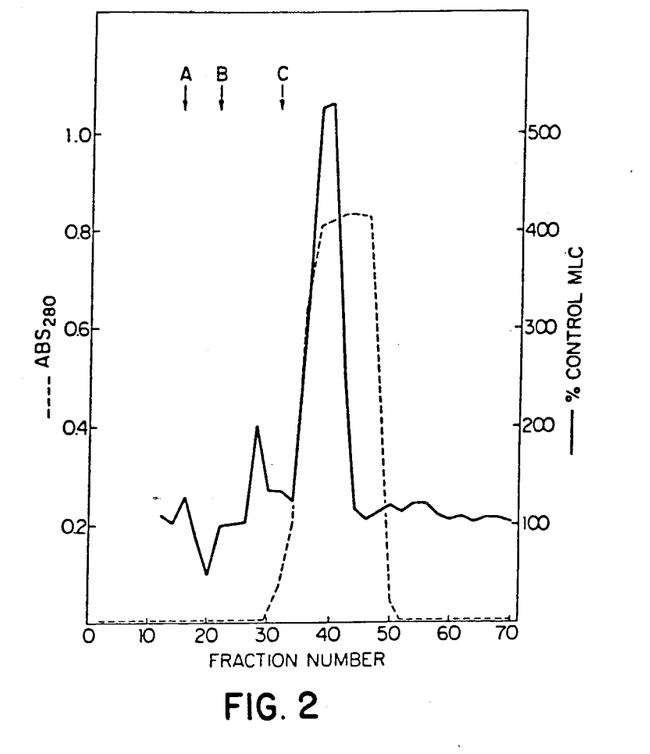
FIG. 2 is a Sephadex G-50 column profile of a G-25 stimulator pool. The Sephadex G-50 column was equilibrated with phosphate buffered saline (PBS). A 5.0 mg sample of the G-25 stimulator pool was applied in 1 ml of PBS. The markers are A, bovine serum albumin; B, cytochrome C; and C, bacitracin. Fractions were screened for absorbance at 280 nm ( - - - ) and for activity in MLC (—).

As shown in FIG. 2, the stimulatory factor is also strongly bound to Sephadex G-50 equilibrated with PBS at pH 7.4. It was observed in this study that the stimulatory factor eluted well beyond the molecular weight appropriate to other thymus factors which have been reported and to interleukin-2. The factor is also distinguished from these factors since they have not been reported to absorb to Sephadex under these conditions. These reports appear in:

Goldstein, G.: Nature 247: 11-14 (1974).

Kook, A. I., Yakir, Y., and Trainin, H.: Cell Immunol. 19: 151-157 (1975).

Dardenne, M., Pleau, J. M., Man, N. K., and Bach, J. F.: J. Biol. Chem 252: 8040-8044 (1977).

Low, T.L.K., Thurman, G. B., Chincanini, C., McClure, J. E., Marshall, G. D., Hu, S. K., and Goldstein, A. L.: Ann. N.Y. Acad. Sci. 332: 33-48 (1979).

Mier, J. W. and Gallow, R. C.: Proc. Natl. Acad. Sci. U.S.A. 77: 6134-6138 (1980).

Gillis, J., Snith, K. A., and Watson, J: J. Immunol. 124: 1954-1962 (1980).

Disabato, G.: Proc. Natl. Acad. Sci. U.S.A. 79: 3020-3023 (1982).

Watson, J., Gillis, S., Marbrook, J., Mochizuki, D., and Smith, K. A.: J. Exp. Med. 150: 849-858.

Thus, at pH 4.5 to 7.4, this stimulatory factor displays a property of chromatographic behavior on Sephadex gels which is distinctly different from previously described thymic or lymphokine factors.

Figure 3:
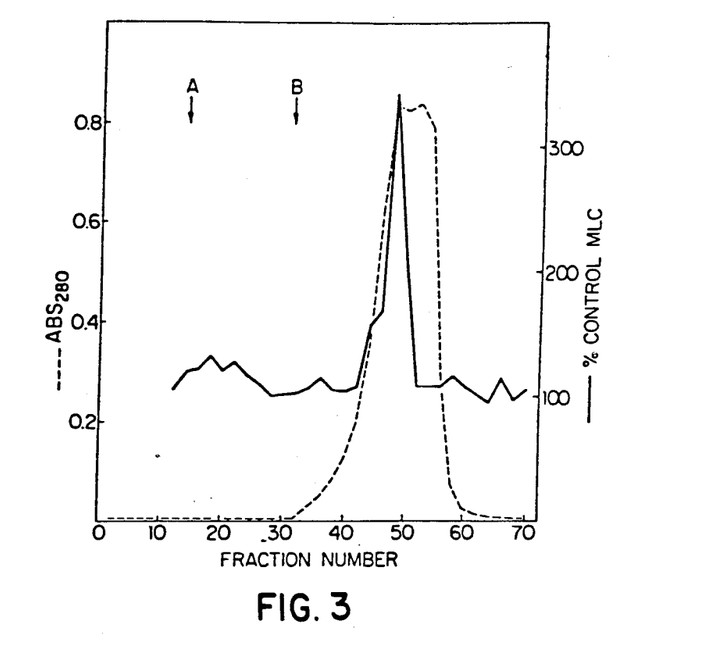
FIG. 3 is a BioGel P-10 column profile of a G-25 stimulator pool. The BioGel P-10 column was equilibrated with 0.5M ammonium bicarbonate, pH 8.0. A 2.7 mg sample of G-25 stimulator pool was applied in 1 ml of elution buffer. The markers are A, bovine serum albumin and B, bacitracin. Fractions were screened for absorbance at 280 nm ( - - - ) and for activity in MLC (—).

A number of peptides possess the property of chemabsorbance on Sephadex gels. One of the techniques for minimizing this is to use a polyacrylamide gel matrix such as BioGel at an alkaline pH as described by Chin and Wold: Anal. Biochem. 16: 585 (1972). A sample of G-25 absorbed material was subjected to chromatography on BioGel P-10 run in 0.5M ammonium bicarbonate, pH 8.0. The elution pattern is shown in FIG. 3. The 280 nm absorbing material was held back under these conditions, similar to the results with the Sephadex G-25 and Sephadex G-50 columns. The stimulatory activity was also held back, indicating the strongly absorbing properties of the stimulatory factor.

From the above, it can be concluded that the stimulatory factor of this invention strongly adheres to any Sephadex at pH 4.5 to 8.0 and to any BioGel at pH 8.0.

Figure 7:
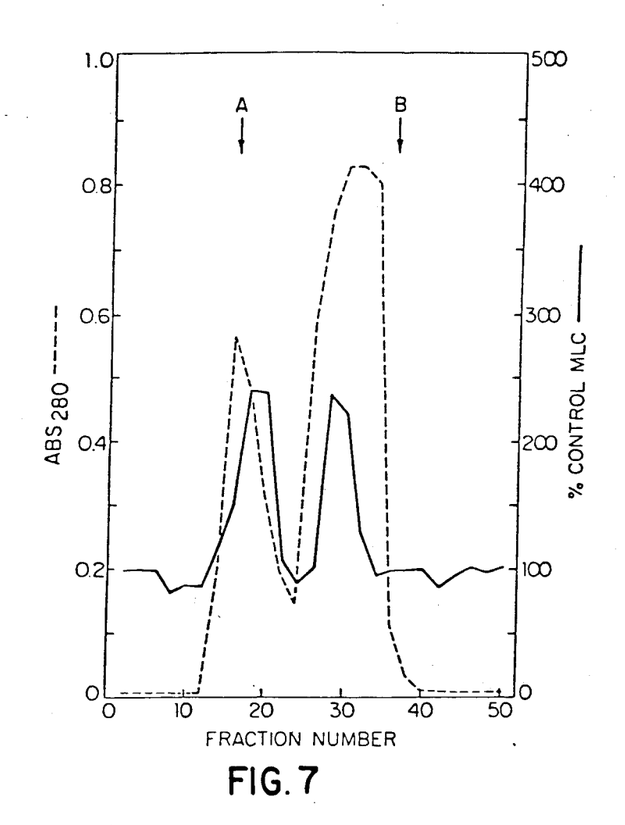
FIG. 7 shows the column profile of the G-25 stimulator pool on BioGel P-2 column. A 10 mg sample of the active pool was applied to a 1×45 cm column of BioGel P-2 equilibrated in 0.05M NH$_4$OH, pH 10.2 and eluted with the same reagent. Fractions were screened for absorbance at 280 nm ( - - - ) and for activity in the MLC assay (—). The markers are A, bovine serum albumin and B, sodium chloride.

When the technique of Chin and Wold was employed under strongly basic conditions, the stimulatory factor eluted before the salt on a BioGel P-2 column as shown in FIG. 7. In this experiment, 10 mg of G-25 stimulatory pool was passed over a 1×45 cm column of BioGel P-2 which had been equilibrated with 0.05M NH$_4$OH, pH 10.2. The fractions were eluted with the same reagent. One result of this treatment is that the factor is split into two fractions. The pattern of FIG. 7 suggests that one of these fractions has a molecular weight of about 1400 Daltons and the other a molecular weight of less than 1400 Daltons but more than 100 Daltons. The significance of the appearance of the two fractions under these strongly basic conditions is not completely understood. It may be that the factor of the invention actually contains two fractions, or that it is split into two fractions by the strong alkaline treatment.

The term 'strongly adheres' as used in this specification and claims means that the factor elutes after a sodium chloride marker on a Sephadex column at pH 4 to 8.

For the dialysis study, a sample of G-25 pool was taken up in 0.1M ammonium acetate, pH 5.0. The Retentate and the Dialysate were freeze dried and assayed by MLC. It was found that 13% of the activity was in the Retentate and 87% of the activity was in the Dialysate. This clearly establishes that the immunostimulatory factor passes through dialysis tubing with a 3500 Dalton cut-off.

Figure 4:
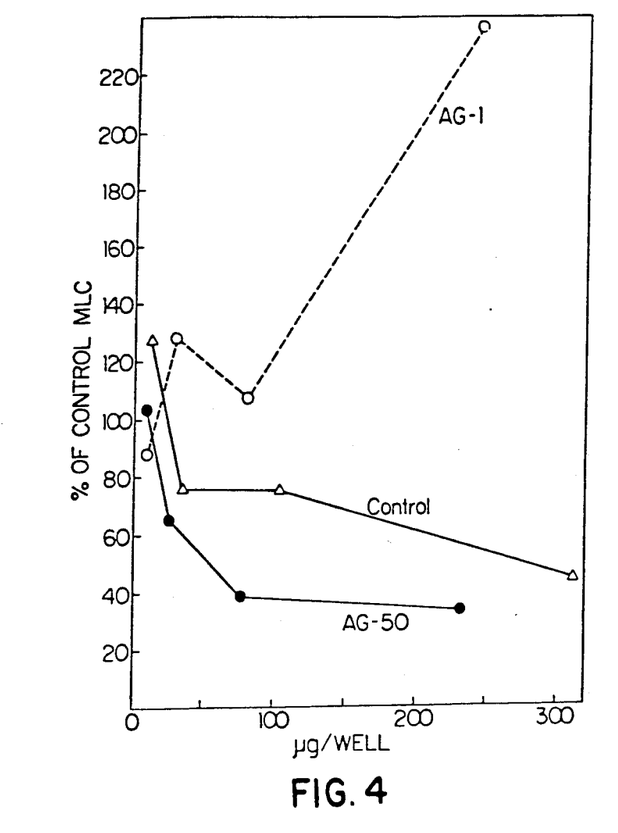
FIG. 4 shows the effect of the passage of a calf thymus extract-acetone precipitate fraction through anion (Ag-1) or cation (AG-50) exchange columns on the ability to inhibit the MLC. AG-1 (o--o) shows the effect observed with the fraction not retained by the AG-1 column; AG-50 (•--•) shows the inhibition observed with the fraction not retained by the AG-50 column. Control ( - - - ) shows the inhibition observed with the untreated sample.

The charge nature of the stimulatory activity has been investigated in several experiments. In the first, the CTE-acetone precipitated material was subjected to analysis on small columns of ion exchange resins. The CTE-acetone precipitated fraction was applied to small columns of either an anion (AG-1) or a cation (AG-50) exchange resin at pH 7. The fraction not retained by the column was examined for its effects on the MLC. As shown in FIG. 4, the fraction not retained by the AG-1 resin significantly stimulated the $^3$H-thymidine incorporation in the MLC. Microscopic examination revealed obvious increases in the number of blast cells at the end of the culture period compared to the control sample. The fraction not retained by the AG-50 column showed an almost threefold increase in total inhibitory activity. This was apparently the result of the removal of stimulatory activity present in the crude CTE-acetone precipitate fraction. This also confirms the results with the G-25 columns which indicated the presence of both stimulatory and inhibitory activity in the extracts.

Figure 5:
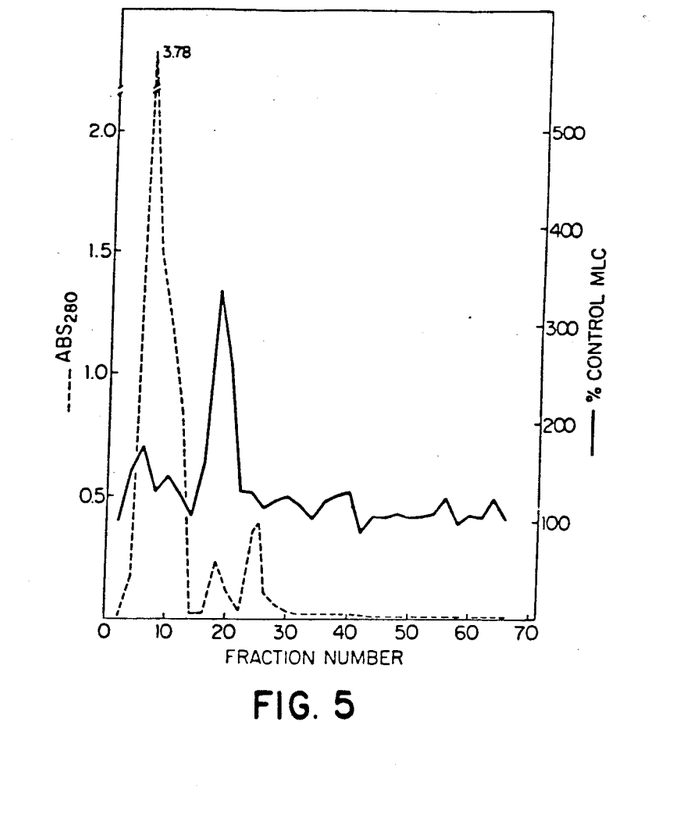
FIG. 5 illustrates ion exchange chromatography of the G-25 stimulator pool. A sample of G-25 stimulator pool, 4.5 mg, was applied to and eluted from a column of BioGel AG-50 ion exchange resin. The fractions were screened for absorbance at 280 nm ( - - - ) and for activity in the MCL (—).

The G-25 stimulatory pool was also subjected to treatment on the ion exchange resin, AG-50, equilibrated with distilled water. The elution profile is shown in FIG. 5. The stimulatory activity was clearly separated from the bulk of the 280 nm absorbing material which was not retarded by the column under these conditions. These results indicate that the stimulatory factor does not bind to an anion exchange resin and is held slightly back by a cation exchange resin. From those results it can be concluded that the stimulatory factor has a neutral or slightly basic isoelectric point, i.e. about 7.0 to 7.8.

The G-25 stimulatory pool increases the DNA-synthetic response of both murine and human lymphocytes to alloantigens in the two-way MLC. The stimulation can be significant, up to five-fold, depending on the culture conditions. The average 2-fold stimulatory dose at the G-25 stage is 10 to 20 $\mu$g/ml for a murine MLC in 10% human serum. As shown in Table 1, the response of murine and human lymphocytes in MLC and of murine lymphocytes to a suboptimal dose of ConA was significantly stimulated. The stimulation of murine lymphocytes by LPS was not significantly increased by the presence of the stimulator. Clearly, the stimulator only works on T-cell mediated responses.

The G-25 stimulatory pool also has an effect on the proliferation of the murine leukemia, L1210, as shown also in Table 1. This indicates that the factor can have a direct mitogenic effect on continuously dividing cells.

TABLE 1

Effect of the G-25 stimulator pool on the lymphocyte proliferative response to antigens and mitogens and on murine leukemic cells.[1]

| Cells | Source | $^3$H—CPM/well S.D. Control | +G-25 Stimulator | % Diff. |
|---|---|---|---|---|
| Lymphocytes | | | | |
| MLC | murine | 36,000 ± 4,700 | 73,400 ± 10,700 | +99 |
| MLC | human | 20,850 ± 2,100 | 45,600 ± 5,100 | +118 |
| Con A | murine | 9,760 ± 1,450 | 8,790 ± 1,170 | −10 |
| Leukemic Cells | | | | |
| L1210 | murine | 40,300 ± 2,300 | 85,900 ± 6,000 | +113 |

[1]Measured by increased counts attributable to tritiated thymidine in blast cells. Each assay was performed with a concentration of G-25 stimulator pool known to cause a 2-fold increase in the $^3$H—thymidine incorporation of a murine, two way MLC in 10% human serum.

Figure 6:
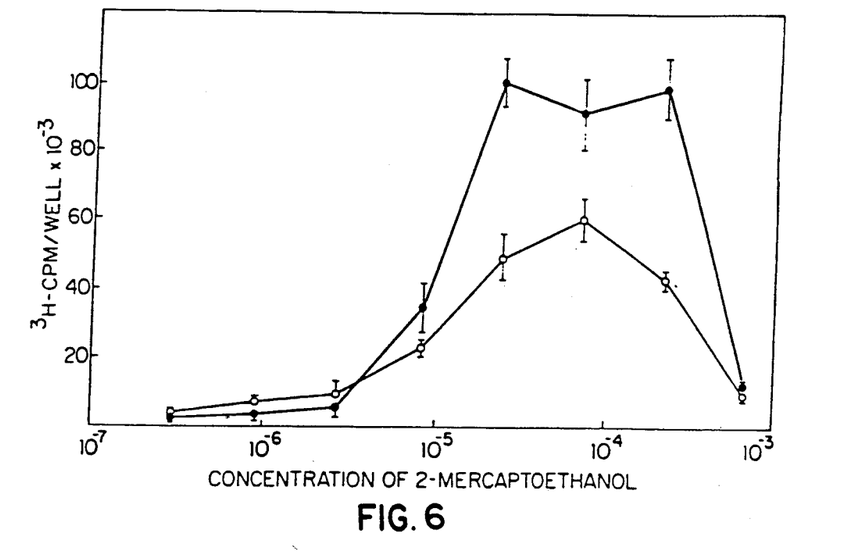
FIG. 6 shows the effect of 2-mercaptoethanol concentration on the activity of the G-25 stimulator pool. A murine MLC was set up at various concentrations of 2-mercaptoethanol and a constant amount of G-25 stimulator pool, 20 µg/ml. The incorporation of $^3$H-thymidine into control cultures (o--o) and G-25 stimulator containing cultures (•--•) was determined.

It has been shown that murine lymphocytes require thiol compounds for maximal response, (Broome et al.: J. Exp. Med. 138: 574 (1973). One way a stimulatory factor could function could be to modify in some way these necessary thiols. To investigate this possibility a murine MLC was set up with various concentrations of 2-mercaptoethanol and contrasted with a concentration of G-25 stimulator pool previously shown to produce a 2-fold stimulation under standard assay conditions. These results are shown in FIG. 6 which indicates that at any 2-mercaptoethanol concentration at which there is a $^3$H-thymidine incorporation significantly above background, that is, a significant response to the alloantigens by the spleen cells, the stimulator increased the response. The stimulator was also active over a wide range of 2-mercaptoethanol concentrations. This shows that alteration of thiol levels is not involved in the action of the stimulator. It also confirms the results with the human MLC which does not require 2-mercaptoethanol in the media for reactivity.

Experiments in which various amounts of the G-25 stimulator pool were added at various times or removed at various times subsequent to the initiation of the MLC are shown in Table 2, 3 and 4. The results show that the action of the stimulator was reversible up until the point that microscopically visible lymphoblast cells are present in the cultures, 72 hr (Tables 2 and 3) and that the stimulator need only be present during the last 24 hr. or less of the culture period (Table 4). All these results are consistent with the target cell of the stimulatory factor being the lymphoblast itself. This clearly distinguishes this factor from other thymic factors which mainly stimulate the maturation of immature T-cells.

It has been observed that the G-25 stimulator pool seemed to work less well in two-way MLCs in medium containing 10% fetal calf serum than in medium containing 10% human serum. When a two-way MLC of murine lymphocytes was conducted in 5% fetal calf serum, under which conditions the total thymidine uptake is about 60% of that which can be demonstrated at 10% fetal calf serum, the stimulator could now increase the total thymidine uptake of these cultures to that observed at 10% serum. In 1% FCS, the G-25 stimulator pool at a concentration of 40 μg/ml could increase the response to that observed in 20% FCS. In this manner, the stimulator can partially replace the serum requirement for the MLC.

It has been shown that mouse serum will inhibit the efficacy of T-cell growth factor, Interleukin-2, Hardt et al. Various concentrations of pooled mouse serum along with various concentrations of the G-25 stimulator pool have been added to two-way murine mixed lymphocyte culture in 5% human serum. There is no evidence that mouse serum at any concentration had an inhibitory effect against the stimulatory ability of any concentration of the stimulatory factor. This serves further to distinguish between the thymic stimulator of this invention and Interleukin-2.

An important aspect of the immune stimulatory factor is its activity in vivo. The ability of the G-25 stimulator pool to accelerate the rejection of histoincompatible skin grafts in mice has been examined. The results are shown in Table 5. At two different doses, the partially purified stimulator significantly accelerated the rejection of the grafts. In the second experiment, the treated mice rejected the grafts at a rate comparable with preimmunized controls. At the doses used, there were no apparent toxic effects.

TABLE 2

REVERSIBILITY OF G-25 STIMULATOR IN MLC AT 24 HR.

| Concentration μg/ml | $^3$H—CPM/Well S.D. (n = 6) | |
|---|---|---|
| | Control | Washed at + 24 hr. |
| 0 | 31,200 ± 1600 | 35,300 ± 2700 |
| 60 | 64,700 ± 7200 | 32,700 ± 2200 |
| 30 | 57,100 ± 4800 | 28,500 ± 2500 |
| 15 | 51,900 ± 5900 | 36,300 ± 3200 |

The reversibility was determined by incubating $1 \times 10^6$ spleen cells of each type in 1.6 ml standard culture media plus or minus the indicated concentration of G-25 stimulator pool in 3 ml plastic culture tubes. After 24 hr., all the tubes were centrifuged at $200 \times g$ for 10 min. to pellet the cells and the media was aspirated from one set of tubes and replaced with an equal volume of prewarmed media without stimulator. These tubes were centrifuged and the media replaced again. After this procedure, the tubes were returned to the incubator for an additional 72 hr. At the end of the incubation, the cells were resuspended and 0.2 ml aliquots placed in microtiter wells for microscopic examination, labeling, and harvesting by the usual procedure.

TABLE 3

REVERSIBILITY OF G-25 STIMULATOR IN MLC

| | $^3$H—CPM/Well S.D. (n = 6) G-25 Stimulator Conc. | |
|---|---|---|
| Treatment | 78 μg/ml | 34 μg/ml |
| Control, no stimulator | 40,100 ± 6300 | 40,100 ± 6300 |
| Control, + stimulator | 67,600 ± 3200 | 86,100 ± 2500 |
| Washed, + 48 hr | 29,800 ± 1600 | 35,900 ± 600 |
| Washed, 72 hr | 44,900 ± 1500 | 46,000 ± 500 |
| Washed, + 96 hr | 58,700 ± 700 | 69,200 ± 1900 |

The reversibility was determined as described under Table 2 except the cells were washed at the indicated times.

TABLE 4

Time course of addition of G-25 Stimulator to MLC

| | $^3$H—CPM/Well S.D. (n = 6) | | | |
|---|---|---|---|---|
| Time of Addition | Control (PBS) | 70 μg/ml | G-25 Stimulator 35 μg/ml | 18 μg/ml |
| 0 | 73,000 ± 7,200 | 167,600 ± 15,600 | 159,500 ± 7,500 | 145,500 ± 800 |
| + 24 hr | 75,400 ± 10,100 | 161,100 ± 8,500 | 150,900 ± 10,100 | 145,700 ± 13,200 |
| + 48 hr | 66,300 ± 7,300 | 173,700 ± 10,000 | 148,100 ± 11,700 | 119,700 ± 7,900 |
| + 72 hr | 67,700 ± 9,600 | 166,500 ± 12,900 | 139,400 ± 21,000 | 105,500 ± 6,500 |

Standard murine MLC assays were set up and the indicated amount of G-25 stimulator pool was added at the indicated time after initiation of the culture. The cells were labeled after the last addition.

TABLE 5

In Vivo Activity of G-25 Stimulator: Acceleration of BALB/c skin graft rejection by C57/BL mice

| Treatment | Day Ave. | Rejected S.D. | Diff. | Sig. |
|---|---|---|---|---|
| A. 40 μg/I.P./Daily | | | | |
| Treated | 9.5 | .4 | 0.8 | .05 |
| Control | 10.3 | .7 | | |
| B. 360 μg/I.P./Daily | | | | |

TABLE 5-continued

In Vivo Activity of G-25 Stimulator: Acceleration
of BALB/c skin graft rejection by C57/BL mice

| Treatment | Day Rejected Ave. | S.D. | Diff. | Sig. |
|---|---|---|---|---|
| Treated | 8.8 | 1.2 | 2.7 | .01 |
| Control | 11.5 | .6 | 2.3 | .005 |
| Pre-immunized control | 9.2 | .8 | | |

Skin grafts were performed as described herein. Treated mice received the indicated amounts of the G-25 stimulator pool. Significance was determined using the Students T-test.

The isolation and biological characterization of a new immunostimulatory factor from bovine thymus has been described. In the presently preferred isolation procedure this factor is extracted from fresh or commercially defatted and dried thymus preparations with a basic buffer followed by solution in 60% ethanol and precipitation by cold acetone. Purification can be effected on Sephadex or BioGel columns at selected hydrogen ion concentrations. The biological activity of the factor, even when only partially purified, resides in its ability to stimulate both the DNA-synthetic response and the number of resulting blast cells of both murine and human T-lymphocytes responding to alloantigen stimulation.

The G-25 stimulator pool had no apparent effect on murine B-lymphocyte response to the polyclonal mitogen LPS. The reversibility experiments described above show that the factor acts very late in the MLC, after or during the formation of morphologically recognizable lymphoblasts in the cultures. The stimulatory effects are totally reversible if the factor is removed before the expiration of 72 hr. of the MLC, but not after 96 hr. In addition, the factor will stimulate the MLC if it is added as late as 72 hr. after start up. The stimulation achieved is equal to the level of stimulation obtained if the factor is continuously present.

The most important biological activity of the factor is the ability to stimulate an in vivo immune response. In the model system employed, the treated mice rejected allogenic grafts at a rate comparable to that of pre-immunized animals. This is probably the maximal rate obtainable in this type of strongly histoincompatible system. It should be noted that these results were obtained in fully immunocompetent, adult mice, responding to a strong antigenic stimulus.

The chemical and biological results described herein show that the stimulatory factor of this invention is distinct from other known thymic hormones and from Interleukin-2. The following Table 6 summarizes the most significant of these distinctions.

TABLE 6

Comparison of some properties of various thymic factors and Interleukin 2[1]

| PROPERTY | G-25 Stim. | FTS[2] | THF[3] | Thymopoietin | Thymosin V | IL-2[4] |
|---|---|---|---|---|---|---|
| MLC[5] | stimulates | no effect | inhibits/stimulates | stimulates | inhibits | stimulates |
| Reversibility[6] at + 24 hr. | yes | no | no | no | no | yes |
| Gel Filtration[7] | Adsorbs | Free | Free | Free | Free | Free |
| Charge[8] | slightly basic | neutral | acidic | acidic | mixture | acidic |

[1]Data are from references mentioned below.
[2]Facteur Thymique Serique - Dardene et al: J. Biol. Chem. 252: 8040 (1977)
[3]Thymic Humoral Factor - Kook et al: Cell Immunol. 19: 151 (1975)
[4]Interleukin 2 or T-cell Growth Factor - Disabato: Proc. Natl. Acad. Sci. U.S.A. 79: 3020 (1982)
[5]Refers to activity in a MLC with either murine, spleen or human peripheral lymphocytes. Several authentic samples of FTS were without effect in MLC system described herein. THF stimulates an MLC only if washed from the cells within 24 hr., if continuously present, THF inhibits
[6]Reversibility determined by washing from cells within 24 hr. or after pre-incubation.
[7]Refers to elution behaviour on various gel filtration supports and under at least one condition mentioned herein.
[8]Refers to the ionic nature determined by isoelectric focusing, electrophoresis, or ion exchange chromatography.

The immunostimulatory factor of this invention can be obtained in highly purified form in accordance with the procedures described herein. However, it is not essential that there be complete purity to achieve the desired therapeutic effect. Compositions containing the factor can be isolated and used alone or in various pharmaceutical compositions to achieve a therapeutic level of the factor in mammalian or avian blood or tissues which is effective to generate an immunostimulatory response.

Several different commercially available factors with immunostimulatory activity were tested in the MLC system. The results of the studies are shown in Table 7. The dosages were selected so as to cover the range which appeared to be optimal based on study of the publications shown in the table and other standard considerations.

TABLE 7

Comparison of the effect of various factors on the standard MLC

| Factor | Dosage | % Increase |
|---|---|---|
| [a]saline | — | — |
| [b]G-25 | 5 µg/ml | +301 |
| [c]IL-2 | 27½ Max units | +43 |
| [d]EGF | 3 ng to 6.7 µg/ml | 0 |
| [e]Thymopoietin II | 30 ng to 67 µg/ml | 0 |
| [f]FTS | 7 ng to 16 µg/ml | 0 |
| [g]FTS + Zn | 7 ng to 16 µg/ml | 0 |
| [h]Tufsin | 70 ng to 167 µg/ml | 0 |

TABLE 7-continued

Comparison of the effect of various factors on the standard MLC

| Factor | Dosage | % Increase |
|---|---|---|
| [i]Levamisole | $1.3 \times 10^{-9}M$ to $2.8 \times 10^{-4}M$ | 0 |

[a]control MLC value with only saline addition
[b]Standard G-25 active immunostimulator pool
[c]Interleukin-2, collaborative Research, obtained from Con A stimulated Rat-Table supernatant by ammonium sulfate precipitation and DEAE-Sephadex. Units as defined by activity against mouse cytotoxic T-lymphocyte line [Rascett et all Blood 57, 399 (1981); Mier et al Proc. Natl. Acad. Sci. U.S.A. 77, 6134 (1980); Di Sabato Proc. Nat. Acad. Sci. U.S.A. 79, 3020 (1982)]
[d]Epidermal Growth Factor, Collaborative Research. No reported immunomodulatory activity but does adsorb to BioGel P-10, Savage et al, J. Biol. Chem. 247, 7609 (1972)
[e]Thymopoietin II active peptide fragment, United States Biochemicals, synthetic peptide [Goldstine Nature (London) 274, 11 (1974); Schlesinger et al, Cell 5, 367 (1974)]
[f] & [g]Facteur Thymique Serique, synthetic peptide, Penninsula Labs. The complex with Zn is the reported active form for the synthetic peptide [Dardenna et al, J. Biol. Chem. 252, 8040 (1977); Bach et al, Trans. Proc. XIV 509 (1982)]
[h]Tufsin, Vega Biochemicals, synthetic tetrapeptide, shown to stimulate macrophages, Nishioka et al, Biochem. Biophys. Res. Comm. 47, 172 (1972)
[i]Levamisole, Sigma Chemical Co., synthetic compound with immunomodulating properties, Hadden, J. W. in The Pharmacology of Immunoregulation. Eds. Werner, G. H. and Floc/h, F. Academic Press, (1978) page 369 et seq.

As will be seen from the table, only the lymphokine IL-2 showed any enhancing effect. In fact, as will be seen from the next table, Table 8, there is a very strong synergistic effect of the two factors.

TABLE 8

Synergistic Effect of G-25 Immunostimulator and IL-2

| | Factor | Concentration | $^3$H—CPM/Well S.D. | % Increase | % Synergy |
|---|---|---|---|---|---|
| (a) | saline control | — | 13,100 ± 1,670 | — | — |
| | G-25 | 15 μg/ml | 44,400 ± 4,000 | 239 | — |
| | IL-2 | 30 U/ml | 25,600 ± 2,300 | 20 | — |
| | G-25 + IL-2 | 15 μg/ml + 30 U/ml | 85,900 ± 16,500 | 556 | 316 |
| (b) | saline control | — | 12,300 ± 1,200 | — | — |
| | G-25 | 33 μg/ml | 30,000 ± 3,100 | 144 | — |
| | IL-2 | 15 U/ml | 18,800 ± 1,300 | 52 | — |
| | G-25 + IL-2 | 33 μg/ml + 15 U/ml | 70,600 ± 5,600 | 474 | 330 |

Standard MLG assays were set-up with the indicated concentrations of each factor. The % increase = 100 × (Experimental cpm-saline control cpm)/saline cpm. The % synergy is defined as 100 × (cpm with G-25 + IL-2-cpm with G-25 alone)/saline control cpm.

It is apparent that compositions containing both the immunostimulatory factor of this invention and IL-2 are valuable for the treatment of patients in need of immunostimulation. Such compositions will typically contain from 10% to 90% by weight of IL-2 based on the total weight of the immunostimulatory factors. The composition may contain any of the usual pharmaceutical excipients.

The products of this invention, that is the factor in highly purified form, salts of the factor or isolated fractions containing the factor, are useful mammalian and avian therapeutic agents and are effective for stimulating an immune response with patients in need of such treatment.

The immunostimulatory factor of this invention is useful for the treatment of any avian or mammalian disease associated with depression of cell mediated immunity. Severe viral, bacterial and fungal infections are often associated with such depression. The factor can be used to enhance the effects of standard therapy normally employed for such infections.

The factor is especially valuable to assist in stimulating the immune response of patients undergoing radiation or chemotherapy for the treatment of malignant diseases.

It is also useful for protecting subjects under such stress as to render them susceptible to infections which they are normally able to resist. Typical examples of such utility are protection of animals against shipping fever, or protection of humans subsequent to surgery.

The physician or veterinarian will determine the dosage which will be most suitable for a particular application. It may vary from patient to patient depending on the size of the patient, the condition under treatment and other factors which are readily evaluated by those skilled in the art. For continuous administration over extended periods to individuals with severe or minor metabolic abnormalities or spleenectomized individuals, the product will normally be provided in various dosage forms varying from relatively large to build up a prompt blood level to relatively small to maintain an effective level. For intermittent treatments to combat acute or chronic infections various dosage forms may be provided.

Normally, the dosage will be in the range of from 0.1 to 0.5 mg/Kg of body weight. To provide these levels, dosage unit forms containing from 0.05 to 0.25 mg of active product can be prepared. Dosage unit forms may, as indicated above, additionally contain from 0.005 to 0.225 mg of IL-2.

The products of this invention may be administered alone but will generally be administered with pharmaceutically acceptable, non-toxic carriers, the proportions of which are determined by the suitability and chemical nature of the particular carrier, the chosen route of administration, and standard pharmaceutical practice. For example, in combatting various infections or in maintaining therapeutically effective levels in the blood or tissue, intravenous or intramuscular administration may be used. The compositions may be in the form of sterile solutions containing other solutes, for example, enough saline or glucose to make them isotonic. Those skilled in the art will know of many standard procedures for preparing such compositions.

An advantage arising from the amphoteric nature of the factor of this invention is that it can be utilized in the form of pharmacologically acceptable salts which may be either metallic salts or acid addition salts. These salts have the advantage of water solubility and are particularly useful for parenteral administration. The metallic salts, especially the alkali metal salts, are relatively stable and for that reason are preferred over acid addition salts. The sodium salts are especially preferred because of their ease of preparation.

The acids which may be used to prepare the pharmacologically acceptable acid addition salts of this invention are those containing non-toxic anions and include, for example, hydrochloric, sulfuric, phosphoric, acetic, lactic, citric, tartaric, oxalic, succinic, maleic, gluconic and saccharic acids.

What is claimed is:

1. An immunostimulator factor isolated from bovine thymus which is a peptide having the properties of:
   A. Strong adherence to Sephadex and BioGel-P at pH 4.5 to 8,
   B. An isoelectric point of about 7.0 to 7.8,
   C. Stimulating the DNA-synthetic response of both murine and human lymphocytes to alloantigenic stimulation in a two way MLC,
   D. Not significantly increasing the stimulation of murine splenic lymphocytes by β-lipopolysaccharides,
   E. Ability to enhance immunostimulatory response even in the presence of 2-mercaptoethanol,
   F. Totally reversible in MLC if removed up to 72 hours from the start of MLC,
   G. Functioning more effectively in MLC containing 10% human serum than in MLC medium containing 10% fetal calf serum,
   H. Ability to enhance immunostimulatory response in MLC even in presence of mouse serum,
   I. Ability to accelerate the rejection of histoincompatible skin grafts in mice,
   J. Ability to pass through dialysis tubing with a 3500 Dalton cut-off,
   K. Splitting into two immunostimulatory fractions, one with a molecular weight of about 1400 Daltons and the other less than 1400 Daltons on gel filtration at pH 10.2 in 0.05M ammonium hydroxide.

2. A process for the preparation of an immunostimulatory factor from bovine thymus comprising the steps of:
   A. Extracting thymus tissue with aqueous buffer at pH 8.5 at about 0° C. to 5° C.,
   B. Centrifuge homogenate at 26,000 to 30,000×g for 20 to 40 minutes at about 0° C. to 5° C.,
   C. Reextract pellet from Step B as in Step A and centrifuge homogenate as in Step B,
   D. Pool supernatants from Steps B and C and lyophilize,
   E. Suspend lyophilized powder in water at about 0° to 5° C. at a concentration of from 0.25 to 0.3 gm/ml and slowly add absolute ethanol with stirring to a final concentration of 50% to 60% (V/V),
   F. Stir for 16 to 18 hours at 0° to 5° C. and centrifuge at 26,000 to 30,000×g for 20 to 40 minutes,
   G. Add supernatant to 5 to 6 volumes of acetone at about −10° C. to −5° C. and let stand for 3 to 6 days at about −10° C. to −5° C.,
   H. Separate precipitate, suspend in about 100 to 200 ml of distilled water or the same amount of about 20 mM acetic acid and lyophilize at 0° to 5° C.,
   I. Dissolve lyophilized powder in buffer at pH 4.5 to 8 and separate over Sephadex or BioGel equilibrated with the same buffer,
   J. Collect fractions and assay by MLC to select the fractions with immunostimulatory activity.

3. A pharmaceutical composition comprising a pharmaceutically acceptable carrier and an amount which is effective to generate an immunostimulatory response of an immunostimulatory factor isolated from bovine thymus which is a peptide having the properties of:
   A. Strong adherence to Sephadex and BioGel-P at pH 4.5 to 8,
   B. An isoelectric point of from 7.0 to 7.8,
   C. Stimulating the DNA-synthetic response of both murine and human lymphocytes to alloantigenic stimulation in a two way MLC,
   D. Not significantly increasing the stimulation of murine splenic lymphocytes by β-lipopolysaccharides,
   E. Ability to enhance immunostimulatory response in the presence of 2-mercaptoethanol,
   F. Totally reversible in MLC if removed up to 72 hours from the start of MLC,
   G. Functioning more effectively in MLC containing 10% human serum than in MLC medium containing 10% fetal calf serum,
   H. Ability to enhance immunostimulatory response in MLC even in presence of mouse serum,
   I. Ability to accelerate the rejection of histoincompatable skin grafts in mice,
   J. Ability to pass through dialysis tubing with a 3500 Dalton cut-off,
   K. Splitting into two immunostimulatory fractions, one with a molecular weight of about 1400 Daltons and the other less than 1400 Daltons on gel filtration at pH 10.2 in 0.05M ammonium hydroxide.

4. A pharmaceutical composition of claim 3 in dosage unit form.

* * * * *

UNITED STATES PATENT AND TRADEMARK OFFICE
CERTIFICATE OF CORRECTION

PATENT NO. : 4,571,336

DATED : February 18, 1986

INVENTOR(S) : John C. Houck et al

It is certified that error appears in the above-identified patent and that said Letters Patent is hereby corrected as shown below:

Column 3, line 11, "in" should read -- is --.

Column 4, line 25, "8,000" should read -- 800 --.

Column 5, line 44, "incomplete" should read -- in complete --.

Column 6, line 19, "in vivo" should be underlined.

Column 6, line 34, "thsi" should read -- this --.

Column 9, line 66, underline "in vivo".

Column 11, line 61, underline "in vivo".

UNITED STATES PATENT AND TRADEMARK OFFICE
CERTIFICATE OF CORRECTION

PATENT NO. : 4,571,336

DATED : February 18, 1986

INVENTOR(S) : John C. HOUCK et al.

It is certified that error appears in the above-identified patent and that said Letters Patent is hereby corrected as shown below:

Column 8, line 56, Table 1, (Page 19, line 9), under the Control Column, "9,760 ± 1,450" should read -- 16,340 ± 1,320 --; under +G-25 Stimulator Column, "8,790 ± 1,170" should read -- 45,080 ± 13,700 --; and under the %Diff. Column, "-10" should read -- +175 --;

Column 8, Table 1, between lines 56 and 57, (Page 19, line 10), insert the following line:

-- LPS murine 9,760 ± 1,450 8,790 ± 1,170 -10 --;

Signed and Sealed this

Second Day of September 1986

[SEAL]

Attest:

Attesting Officer

DONALD J. QUIGG

Commissioner of Patents and Trademarks